United States Patent [19]
Kaneko et al.

[11] Patent Number: 6,008,239
[45] Date of Patent: Dec. 28, 1999

[54] TRIAZOLE DERIVATIVE OR SALT THEREOF

[75] Inventors: Yasushi Kaneko, Narita; Sunao Takeda, Ichihara; Minoru Tokizawa, Narita; Hiromichi Eto, Narita; Kazuya Ishida, Narita; Kazunori Maebashi, Narashino; Masaru Matsumoto, Chiba; Takemitsu Asaoka; Susumu Sato, both of Narita, all of Japan

[73] Assignee: SSP Co., Ltd., Tokyo, Japan

[21] Appl. No.: 09/135,163

[22] Filed: Aug. 17, 1998

[30] Foreign Application Priority Data

Aug. 29, 1997 [JP] Japan .................................. 9-234546

[51] Int. Cl.$^6$ ....................... A61K 31/505; C07D 249/08
[52] U.S. Cl. ......................... 514/383; 548/268.6
[58] Field of Search ........................... 514/383; 548/268.6

[56] References Cited

FOREIGN PATENT DOCUMENTS

| | | |
|---|---|---|
| 113640 | 7/1984 | European Pat. Off. . |
| 0 117 100 | 8/1984 | European Pat. Off. . |
| 0 473 387 | 3/1992 | European Pat. Off. . |
| 0 780 380 | 6/1997 | European Pat. Off. . |
| 0 814 079 | 12/1997 | European Pat. Off. . |

OTHER PUBLICATIONS

Patent Abstracts of Japan, vol. 18, No. 639 (C–1282), Dec. 6, 1994, JP 06 247944, Sep. 6, 1994.

*Primary Examiner*—Patricia L. Morris
*Attorney, Agent, or Firm*—Oblon, Spivak, McClelland, Maier & Neustadt, P.C.

[57] ABSTRACT

Described is a triazole derivative represented by the formula (1):

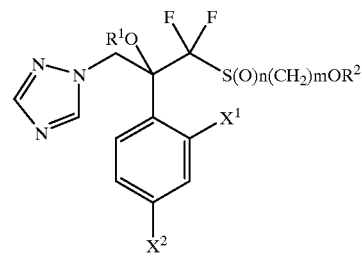

(1)

wherein $R^1$ represents a lower alkyl group or an aralkyl group, $R^2$ represents a hydrogen atom, a lower alkyl group, an aralkyl group or an acyl group, $X^1$ and $X^2$ are the same or different and each independently represents a hydrogen atom, a halogen atom or a trifluoromethyl group, n stands for an integer of 0 to 2 and m stands for an integer of 1 to 5, or salt thereof; and also a pharmaceutical comprising the derivative or salt thereof as an effective ingredient. The compound as described above has a high antimycotic activity and is useful for the prevention and treatment of mammalian mycotic infections.

7 Claims, No Drawings

TRIAZOLE DERIVATIVE OR SALT THEREOF

TECHNICAL FIELD

This invention relates to a triazole derivative or salt thereof which has excellent antimycotic activity and high safety and a pharmaceutical comprising the same as an effective ingredient.

BACKGROUND ART

Mycosis can be classified into two types, that is, superficial mycosis represented by various trichophytosis, marginated eczema, psoriasis, cutaneous candidiasis or the like and deep seated mycosis represented by mycotic meningitis, mycotic infectious disease of respiratory organ, fungemia, mycosis of urinary tract or the like. Of these, deep seated mycosis such as candidiasis or aspergillosis tends to show a marked increase in recent days owing to the frequent use of an anticancer chemotherapeutic agent or immunosuppressive agent or lowering in the bioimmunology due to HIV infection or the like. There is accordingly a demand for a pharmaceutical efficacious against fungi causing such diseases. At present, pharmaceuticals effective against Aspergillus spp. and Candida spp. are not so many. As a remedy for such deep seated mycosis, Amphotericin B and azole-based compounds such as Fluconazole and Itraconazole are conventionally known, but they involve problems in safety and antimycotic activity. There is accordingly a demand for an antimycotic effective against Aspergillus spp. and Candida spp. Now, more effective azole-based compounds are under development. For example, as a compound having a hydroxyethyl group, compounds described in Japanese Patent Application Laid-Open No. 247944/1994 or the like and as a compound having a difluoromethylene group, those described in Japanese Patent Application Laid-Open No. 163374/1984, Japanese Patent Application Laid-Open No. 163269/1993 or the like are known. As an azole-based compound having a substituted tertiary hydroxyl group, cyclic compounds as described in Japanese Patent Application Laid-Open Nos. 217778/1996 and 333367/1996, acyl compounds as described in Japanese Patent Application Laid-Open Nos. 104676/1996 and 183769/1997, and the like are known but they are not fully satisfactory.

Accordingly, an object of the present invention is to provide a compound which has high safety and has antimycotic activity effective against Aspergillus spp. and Candida spp.

DISCLOSURE OF THE INVENTION

With the forgoing in view, the present inventors synthesized a number of triazole derivatives and salts thereof and carried out an investigation on their antimycotic activity effective against Aspergillus spp. and Candida spp. As a result, it has been found that a triazole derivative represented by the below-described formula (1) and a salt thereof have excellent antimycotic activity against fungi including Aspergillus spp. and Candida spp. and at the same time have high safety, leading to the completion of the present invention.

In one aspect of the present invention, there is thus provided a triazole derivative represented by the following formula (1):

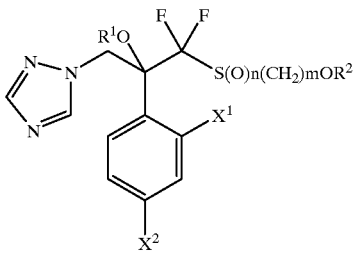

wherein $R^1$ represents a lower alkyl or aralkyl group, $R^2$ represents a hydrogen atom or a lower alkyl, aralkyl or acyl group, $X^1$ and $X^2$ are the same or different and each independently represents a hydrogen atom, a halogen atom or a trifluoromethyl group, n stands for an integer of 0 to 2 and m stands for an integer of 1 to 5; or salt thereof.

In another aspect of the present invention, there is also provided a pharmaceutical comprising the triazole derivative (1) or salt thereof as an effective ingredient.

In a further aspect of the present invention, there is also provided a pharmaceutical composition comprising the triazole derivative (1) or salt thereof and a pharmacologically acceptable carrier.

In a still further aspect of the present invention, there is also provided the use of the triazole derivative (1) or salt thereof as a pharmaceutical.

In a still further aspect of the present invention, there is also provided a treating method of mycotic infections, which comprises administering to a patient an effective amount of the triazole derivative (1) or salt thereof.

BEST MODES FOR CARRYING OUT THE INVENTION

In the triazole derivative (1) of the present invention, examples of the lower alkyl group of $R^1$ or $R^2$ include linear or branched $C_{1-6}$ alkyl groups. Specific examples include methyl, ethyl, n-propyl, isopropyl, n-butyl, tertbutyl, pentyl and hexyl. Among them, $C_{1-4}$ alkyl groups are more preferred, with a methyl group being particularly preferred.

Examples of the halogen atom of $X^1$ or $X^2$ include fluorine, chlorine, bromine and iodine atoms.

Examples of the aralkyl group of $R^1$ or $R^2$ include $C_{7-11}$ aralkyl groups. Among them, phenyl-$C_{1-5}$-alkyl groups are more preferred and specific examples include benzyl and phenethyl.

Examples of the acyl group of $R^2$ include $C_{2-10}$ acyl groups, $C_{2-10}$ alkanoyl groups such as acetyl, propanoyl and octanoyl and $C_{7-10}$ aroyl groups such as benzoyl. Among them, in the present invention, $C_{2-10}$ alkanoyl groups are more preferred, with an acetyl group being particularly preferred.

In the triazole derivative (1) of the present invention, preferred as $R^1$ are methyl, ethyl and benzyl groups, with the methyl group being particularly preferred. Preferred as $R^2$ are a hydrogen atom and methyl, benzyl and acetyl groups, with the methyl group being particularly preferred. As $X^1$ or $X^2$, a halogen atom is preferred, with the fluorine atom being particularly preferred. Preferred as n are 0 and 2, while preferred as m are 1 to 3, with 2 being particularly preferred.

No particular limitation is imposed on the salt of the triazole derivative (1) of the present invention insofar as it is a pharmacologically acceptable salt. Examples include acid addition salts such as hydrochloride, nitrate, hydrobromide, p-toluenesulfonate, methanesulfonate, fumarate, succinate and lactate.

The triazole derivative (1) or salt thereof according to the present invention has optical activity based on the asymmetric carbon. The present invention therefore embraces racemic modifications and optically active substances. The present invention also embraces hydrates of these compounds.

The triazole derivative (1) or salt thereof according to the present invention can be prepared, for example, in accordance with the reaction scheme described below:

Compound (4), fluorinating the resulting Compound (3) or (4) into Compound (5), epoxydizing the resulting Compound (5) into Compound (6), and then introducing a triazole group into Compound (6). Compound (4) is also available by directly introducing an alkyloxyalkylthio, aralkyloxyalkylthio or acyloxyalkylthio group into Compound (2). Invention Compound (1a) can be obtained by alkylation of Compound (7) and the resulting Compound (1a) can be converted into the invention Compound (1b) by oxidation.

Described more specifically, Compound (3) can be prepared by introducing a hydroxyalkylthio group into

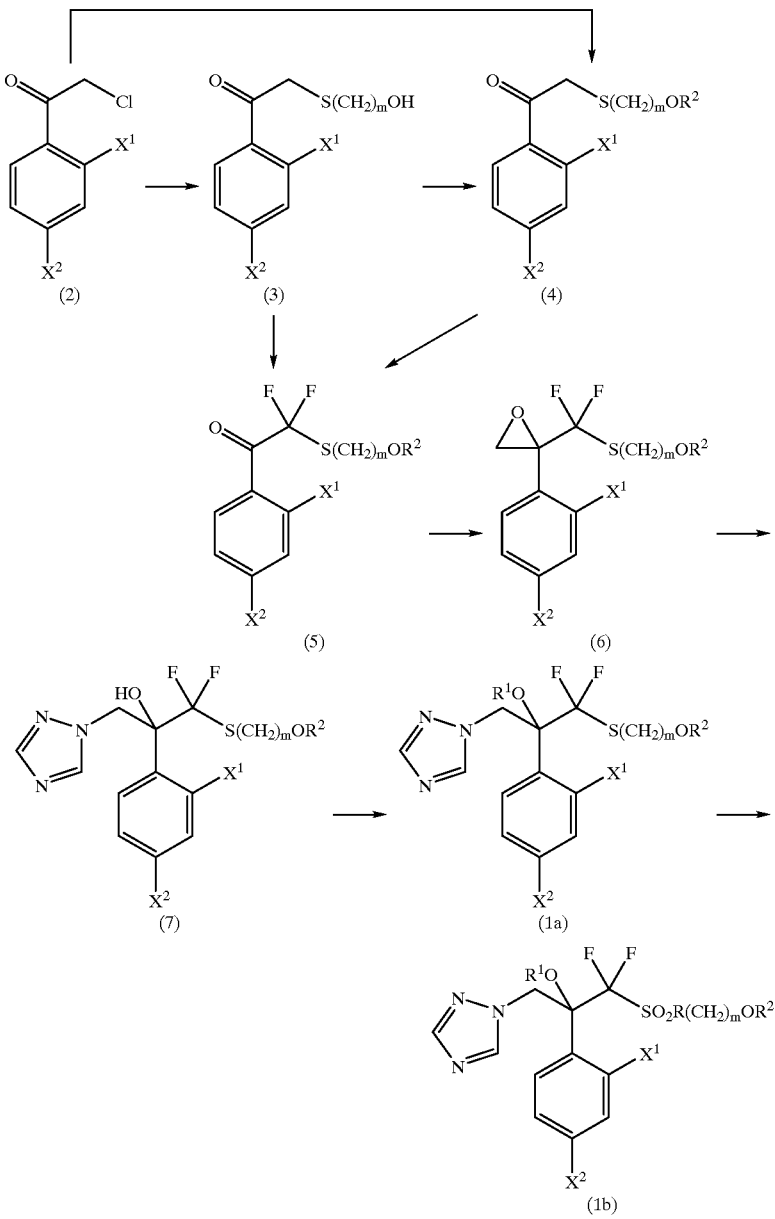

wherein $R^1$, $R^2$, $X^1$, $X^2$ and m have the same meanings as defined above.

Described specifically, Compound (7) can be prepared by introducing a hydroxyalkylthio group into Compound (2), thereby forming Compound (3), subjecting the resulting Compound (3) to alkylation, aralkylation or acylation into 2-chloro-2',4'-difluoroacetophenone (2) put on the market, for example, by Aldrich Chemical Co., Inc. As a hydroxyalkylthio-introducing reagent, ω-mercaptoalcohols such as 2-mercaptoethanol are usable. As a base, sodium hydroxide, potassium hydroxide, barium hydroxide, sodium carbonate, potassium carbonate, sodium hydride (NaH) or the like is usable. Examples of a solvent usable here include alcoholic solvents such as methanol and ethanol, nonaqueous polar solvents such as N,N-dimethylformamide (DMF) and etheric solvents such as 1,4-dioxane and tetrahydrofuran (THF), with the methanol being preferred. The reaction temperature is −40° C. to the boiling point of the solvent, with 20 to 60° C. being preferred.

Compound (4) can be prepared by subjecting Compound (3) to alkylation, aralkylation or acylation in a solvent. Examples of the alkylating reagent usable here include alkyl halides such as methyl iodide and propyl iodide and sulfate esters such as dimethyl sulfate, those of the aralkylating reagent include aralkyl halides such as benzyl bromide and phenethyl chloride; and those of the acylating reagent include acyl halides such as acetyl chloride and propionyl chloride and acid anhydrides such as acetic anhydride. As the solvent, it is possible to use a basic solvent such as pyridine singly or to use a hydrocarbon base solvent such as benzene or toluene or an etheric solvent such as diethyl ether or tetrahydrofuran in the presence of a base typified by potassium carbonate or sodium hydroxide. The reaction temperature is at −40° C. to the boiling point of the solvent, with 20 to 60° C. being preferred.

Compound (4) can also be prepared by introducing an alkyloxyalkylthio, aralkyloxyalkylthio or acyloxyalkylthio group directly into 2-chloro-2',4'-difluoroacetophenone (2). Described specifically, Compound (4) can be prepared, for example, by reacting 2-chloro-2',4'-difluoroacetophenone (2) with an alkyloxyalkylthiol such as 2-methyloxyethanethiol (J. Med. Chem., 39, 1253(1966)), an aralkyloxyalkylthiol such as benzyloxyethanethiol prepared similarly or an acyloxyalkylthiol such as 2-acetoxyethanethiol (J. Chem. Soc., 817(1952)) in the presence of a base such as sodium hydroxide, potassium hydroxide, barium hydroxide, sodium carbonate, potassium carbonate or sodium hydride in a solvent such as an alcoholic solvent, e.g., methanol or ethanol, a nonaqueous polar solvent, e.g., N,N-dimethylformamide or an etheric solvent such as 1,4-dioxane or tetrahydrofuran. Potassium carbonate and methanol can be given as the preferred examples of the base and solvent, respectively. The reaction temperature is −40° C. to the boiling point of the solvent, with 20 to 60° C. being preferred.

Compound (5) can be prepared by reacting Compound (3) or Compound (4) with a halogenating reagent in a solvent. A fluorinating agent is preferred as the halogenating reagent. Examples of the fluorinating agent include fluorine gas, perchloryl fluoride, potassium fluoride, spray-dried potassium fluoride, freeze-dried potassium fluoride, tetraalkylammonium fluoride, tris(dimethylamino)sulfa(trimethylsilyl) difluoride, N-fluoropyridone, N-fluoro-N-alkyl-arenesulfonamide, N-fluoroquinuclidinium salt, N-fluoroperfluoroalkyl sulfonimide, N-fluorosaltum, fluorinated xenon, N-fluoropyridinium salt and N-fluoropyridinium sulfonate. Examples of the commercially available fluorinating reagent include "Onoda Fluorinates FP-T300, FP-T500, FP-T700, FP-B300, FP-B500, FP-B700 and FP-B800" (trade names; products of Chichibu Onoda Co., Ltd.) and "MEC-01, MEC-02, MEC-03, MEC-04 and MEC-05" (trade names; products of Daikin Industries, Ltd.). It is preferred to use the fluorinating reagent in an amount of 2 to 20 equivalents per mole of Compound (4). Illustrative of the solvent include 1,2-dichloroethane, 1,1,2-trichloroethane, chloroform, methylene chloride, diethyl ether, ethyl acetate and tetrahydrofuran. Among them, 1,1,2-trichloroethane can be used suitably. The reaction temperature is −78° C. to the boiling point of a solvent, with 80 to 100° C. being preferred. To improve the yield of the compound, a Lewis acid or a base can be used. Exemplary Lewis acids include aluminum chloride, zinc chloride and tin chloride, while exemplary bases include sodium hydroxide, potassium hydroxide, barium hydroxide, sodium carbonate, potassium carbonate, sodium hydride, potassium tert-butoxide, lithium diisopropylamide and potassium hexamethyldisilazane.

Compound (6) can be prepared by reacting Compound (5) with 1 to 2 equivalents of an epoxymethylating reagent such as trimethylsulfoxonium iodide or trimethylsulfonium iodide in the presence of 2 to 5 equivalents of an alkali. As the solvent, dimethylsulfoxide (DMSO), tetrahydrofuran or the like can be used suitably. Examples of the base include sodium hydroxide, potassium hydroxide, barium hydroxide, sodium carbonate, potassium carbonate, sodium hydride and sodium methoxide, with sodium hydride being particularly preferred. The reaction temperature is −100° C. to the boiling point of the solvent, with −40 to 50° C. being preferred.

Compound (7) can be prepared by reacting Compound (6) with 1,2,4-triazole or an alkali metal salt thereof in a solvent in the presence of a base. As the solvent, N,N-dimethylformamide, acetonitrile, N,N-dimethylacetamide or dimethylsulfoxide can be used suitably. Examples of the base usable here include sodium hydroxide, potassium hydroxide, barium hydroxide, sodium carbonate, potassium carbonate or potassium tert-butoxide. The reaction temperature is 0° C. to the boiling point of the solvent, with 20 to 60° C. being preferred.

Compound (1a) can be prepared by alkylating Compound (7) by using an alkyl halide or the like in the presence of a base. Examples of the alkyl halide include methyl iodide, ethyl iodide, propyl iodide and benzyl chloride. Examples of the base include sodium hydroxide, potassium hydroxide, barium hydroxide, sodium carbonate, potassium carbonate and sodium hydride (NaH). Examples of the solvent include alcoholic solvents such as methanol and ethanol, nonaqueous polar solvents such as N,N-dimethylformamide (DMF) and etheric solvents such as 1,4-dioxane and tetrahydrofuran (THF), with the DMF being preferred. The reaction temperature is −40° C. to the boiling point of the solvent, with 0 to 20° C. being preferred.

Compound (1b) can be prepared by oxidizing Compound (1a) with at least 2 equivalents, preferably 2.2 to 2.3 equivalents of an oxidizing agent. Examples of the oxidizing agent include m-chloroperbenzoic acid, aqueous hydrogen peroxide, peracetic acid, tetrapropylammonium perruthenate, osmium tetraoxide, potassium permanganate and oxone. Illustrative of the usable solvent include chloroform, dichloromethane, acetic acid, methanol, water, acetonitrile and carbon tetrachloride, and mixtures thereof. The reaction temperature is −40° C. to the boiling point of the solvent, with 0 to 50° C. being preferred. To improve the yield, ruthenium trichloride, selenium dioxide, sodium tungstate, sodium molybdate and vanadium oxide can be used as a catalyst.

No particular limitation is imposed on the isolation means of a target product from the reaction mixture available by each of the above-described reactions. The target product can be isolated, for example, by recrystallization, various types of chromatography or the like. Moreover, the target compound can be converted into a desired salt in a manner known per se in the art.

The invention Compound (1) or salt thereof so obtained has excellent in vivo or in vitro antimycotic action against fungi including Aspergillus spp. and Candida spp. and at the same time has high safety so that it is useful as a pharmaceutical for the prevention and treatment of various mycotic infections.

From the invention compound, a pharmaceutical composition can be obtained in various dosage forms such as tablets, granules, powders, capsules, suspensions, injections, suppositories and external preparations in a conventional manner by adding a pharmacologically acceptable carrier to the invention compound as needed. It is preferred for the preparation of a solid preparation that after an excipient and, if necessary, a binder, disintegrator, extender, coating agent, sugar-coating agent and/or the like are added to the invention compound, the resulting mixture is formed into tablets, granules, capsules, suppositories or the like in a manner known per se in the art. For the preparation of an injection, it is only necessary to dissolve, disperse or emulsify the invention compound in an aqueous carrier such as distilled water for injection in advance or to prepare powder for injection and dissolve it upon use. Examples of the administration method of the injection include intravenous administration, intraarterial administration, intraperitoneal administration, subcutaneous administration and instillation.

The dose of the invention compound differs depending on the administration method, symptoms, weight and age of the patient to be administered but administration of 0.1 to 100 mg/day per adult is preferred.

EXAMPLES

The present invention will hereinafter be described in detail by Examples. It should however be borne in mind that the present invention will not be limited to or by the following examples.

Referential Example 1

Synthesis of 2',4'-difluoro-2-(2-methoxyethyl)thioacetophenone

To a solution of 2-chloro-2',4'-difluoroacetophenone (2.7 g, 0.014 mol) and 2-methoxyethanethiol (J. Med. Chem., 39, 1253(1996)) (1.4 g, 0.015 mol) in methanol (50 ml), potassium carbonate (2.3 g, 0.016 mol) was added under ice cooling, followed by stirring at room temperature for 30 minutes. After the completion of the reaction, the insoluble matter was filtered off and the filtrate was distilled off under reduced pressure. The residue so obtained was diluted with ether, washed with water, dried over magnesium sulfate and distilled off under reduced pressure, whereby 2',4'-difluoro-2-(2-methoxyethyl)thioacetophenone (2.3 g, yield: 67.0%) was obtained as a colorless oil.

$^1$H-NMR (CDCl$_3$) δ: 2.71(2H,t,J=6.4 Hz), 3.38(3H,s), 3.56(2H,t,J=6.4 Hz), 3.84(2H,d,J=2.4 Hz), 6.7-7.1(2H,m), 7.7-8.1(1H,m).

Referential Example 2

Synthesis of 2,2-difluoro-2',4'-difluoro-2-(2-methoxyethyl)thioacetophenone

To a solution of 2',4'-difluoro-2-(2-methoxyethyl)thioacetophenone (1.00 g, 0.004 mol) in 1,1,2-trichloroethane (50 ml), N-fluoro-4-methylpyridinium-2-sulfonate ("MEC-02", produced by Daikin Industries, Ltd.) (2.17 g, 0.011 mol) was added in portions at an internal temperature of 85° C., followed by stirring at an internal temperature of 100 to 110° C. for 2 hours. After the completion of the reaction, the reaction mixture was diluted with ethyl ether and an insoluble matter was filtered off. The ether solution was washed with water, dried over magnesium sulfate and distilled off under reduced pressure. The residue so obtained was subjected to chromatography on a silica gel column, whereby from the fraction eluted with chloroform, 2,2-difluoro-2',4'-difluoro-2-(2-methoxyethyl)thioacetophenone (0.43 g, yield: 39.0%) was obtained as a pale yellow oil.

$^1$H-NMR (CDCl$_3$) δ: 3.08(2H,t,J=6.2 Hz), 3.46(3H,s), 3.64(2H,t,J=6.2 Hz), 6.7-7.1(2H,m), 7.7-8.1(1H,m).

Referential Example 3

Synthesis of 2-(2,4-difluorophenyl)-1,1-difluoro-1-[(2-methoxyethyl)thiol]-2,3-epoxypropane A suspension of 60% NaH (2.2 g, 0.055 mol) in THF (60 ml)-DMSO (120 ml) was heated to an external temperature of 50° C., followed by the addition of trimethylsulfoxonium iodide (12.1 g, 0.055 mol) in portions. The resulting mixture was stirred for 15 minutes at the same temperature and then cooled to −20° C. To the reaction mixture, a solution of 2,2-difluoro-2',4'-difluoro-2-(2-methoxyethyl)thioacetophenone (13.0 g, 0.046 mol) in THF (60 ml) was added dropwise and the resulting mixture was stirred for 1.5 hours at room temperature. The reaction mixture was poured into ice water, followed by extraction with ether. The ether solution was washed with water, dried over magnesium sulfate and then distilled off under reduced pressure, whereby 2-(2,4-difluorophenyl)-1,1-difluoro-1-[(2-methoxyethyl)thio]-2,3-epoxypropane (13.0 g, yield: 95.4%) was obtained as a pale yellow oil.

$^1$H-NMR (CDCl$_3$) δ: 2.6–2.8(1H,m), 3.01(2H,t,J=6.4 Hz), 3.35(3H,s), 3.4–3.7(3H,m), 6.6–7.1(2H,m), 7.4–7.7 (1H,m).

Referential Example 4

Synthesis of 2-(2,4-difluorophenyl)-1,1-difluoro-1-[(2-methoxyethyl)thio]-3-(1H-1,2,4-triazol-1-yl)-2-propanol To a solution of 2-(2,4-difluorophenyl)-1,1-difluoro-1-[(2-methoxyethyl)thio]-2,3-epoxypropane (13.0 g, 0.044 mol) in DMSO (100 ml), 1,2,4-triazole (7.6 g, 0.11 mol) and potassium carbonate (15.2 g, 0.11 mol) were added and the resulting mixture was stirred at room temperature for 12 hours and at an external temperature of 50° C. for one hour. After the completion of the reaction, the reaction mixture was diluted with ether and insoluble matter was filtered off. The ether solution was washed with water, dried over magnesium sulfate and distilled off under reduced pressure. The residue was recrystallized from isopropyl ether-ethyl acetate, whereby 2-(2,4-difluorophenyl)-1,1-difluoro-1-[(2-methoxyethyl)thio]-3-(1H-1,2,4-triazol-1-yl)-2-propanol (2.0 g, yield: 12.0%) was obtained as colorless crystals.

Melting point: 80–81° C.

IR(KBr) $v_{max}$cm$^{-1}$: 1130

MS (FAB): 366 (M+H)

$^1$H-NMR (CDCl$_3$) δ: 3.01(2H,t,J=6.6 Hz), 3.35(3H,s), 3.58(2H,t,J=6.6 Hz), 4.81(1H,d,J=14.5 Hz), 5.29(1H,d,J=14.5 Hz), 5.80(1H,s), 6.5–6.9(2H,m), 7.6–7.9(1H,m), 7.80 (1H,s), 8.09(1H,s).

Example 1

Synthesis of 1-{2-(2,4-difluorophenyl)-3,3-difluoro-2-methoxy-3-[(2-methoxyethyl)thio]propyl}-1H-1,2,4-triazole To a solution of 60% sodium hydride (131 mg, 3.29 mmol) in N,N-dimethylformamide (50 ml), 2-(2,4- difluorophenyl)-1,1-difluoro-1-[(2-methoxyethyl)thio]-3-(1H-1,2,4-triazol-1-yl)-2-propanol (1.0 g, 2.74 mmol) was added dropwise under ice cooling. The resulting mixture was stirred at room temperature for 30 minutes. To the reaction mixture, methyl iodide (516 mg, 3.56 mmol) was added dropwise under ice cooling and the resulting mixture was stirred at room temperature for one hour. Water was added to the reaction mixture and the resulting mixture was extracted with ethyl acetate. The ethyl acetate solution was washed with water, dried over anhydrous sodium sulfate and then distilled off under reduced pressure. The residue was separated and purified by a silica gel column (chloroform:n-hexane=50:1), whereby 1-{2-(2,4-difluorophenyl)-3,3-difluoro-2-methoxy-3-[(2-methoxyethyl)thio]propyl}-1H-1,2,4-triazole (894 mg, yield: 86.0%) was obtained as a yellow oil.

MS(FAB): 380 (M+H)

$^1$H-NMR (CDCl$_3$) δ: 2.97(2H,t,J=7 Hz), 3.34(3H,s), 3.56 (2H,t,J=7 Hz), 3.73(3H,t,J=2 Hz), 5.09(2H,t,J=15 Hz), 6.6–6.9(2H,m), 7.4–7.7(1H,m), 7.79(1H,s), 7.99(1H,s).

Example 2

1-[3-{[2-(Benzyloxy)ethyl]thio}-2-(2,4-difluorophenyl)-3,3-difluoro-2-methoxypropyl]-1H-1,2,4-triazole In a similar manner to Example 1 except that 1-{[2-(benzyloxy)ethyl]thio}-2-(2,4-difluorophenyl)-1,1-difluoro-3-(1H-1,2,4-triazol-1-yl)-2-propanol was used instead of 2-(2,4-difluorophenyl)-1,1-difluoro-1-[(2-methoxyethyl)thio]-3-(1H-1,2,4-triazol-1-yl)-2-propanol, the experiment was carried out, whereby 1-[3-{[2-(benzyloxy)ethyl]thio}-2-(2,4-difluorophenyl)-3,3-difluoro-2-methoxypropyl]-1H-1,2,4-triazole was obtained as a colorless oil.

MS(FAB): 456(M+H)

$^1$H-NMR (CDCl$_3$) δ: 2.99(2H,t,J=6 Hz), 3.64(2H,t,J=6 Hz), 3.71(3H,s), 4.50(2H,s), 5.07(2H,br.s), 6.64–6.90(2H, m), 7.64(5H,s), 7.47–7.64(1H,m), 7.77(1H,s), 7.98(1H,s).

Example 3

2-{[2-(2,4-difluorophenyl)-1,1-difluoro-2-methoxy-3-(1H-1,2,4-triazol-1-yl)propyl]thio}-1-ethanol In a similar manner to Example 1 except that 2-(2,4-difluorophenyl)-1,1-difluoro-1-[(2-methoxyethyl)thio]-3-(1H-1,2,4-triazol-1-yl)-2-propanol was replaced with 2-(2,4-difluorophenyl)-1,1-difluoro-1-[(2-hydroxyethyl)thio]-3-(1H-1,2,4-triazol-1-yl)-2-propanol, the experiment was carried out, whereby 2-{[2-(2,4-difluorophenyl)-1,1-difluoro-2-methoxy-3-(1H-1,2,4-triazol-1-yl)propyl]thio}-1-ethanol was obtained as colorless crystals.

Melting point: 76–79° C.

IR(KBr)ν$_{max}$cm$^{-1}$: 3111, 1612, 1506, 1132

MS(FAB): 366(M+H)

$^1$H-NMR(CDCl$_3$) δ: 2.98(2H,t,J=5.9 Hz), 3.5–4.0(5H,m), 5.09(2H,s), 6.6–7.0(2H,m), 7.4–7.8(1H,m), 7.81(1H,s), 7.99 (1H,s).

Example 4

2-{[2-(2,4-Difluorophenyl)-2-ethoxy-1,1-difluoro-3-(1H-1,2,4-triazol-1-yl)propyl]thio}-1-ethanol In a similar manner to Example 1 except that 2-(2,4-difluorophenyl)-1,1-difluoro-1-[(2-methoxyethyl)thio]-3-(1H-1,2,4-triazol-1-yl)-2-propanol was replaced with 2-(2,4-difluorophenyl)-1,1-difluoro-1-[(2-hydroxyethyl)thio]-3-(1H-1,2,4-triazol-1-yl)-2-propanol and methyl iodide was replaced with ethyl iodide, the experiment was carried out, whereby 2-{[2-(2,4-difluorophenyl)-2-ethoxy-1,1-difluoro-3-(1H-1,2,4-triazol-1-yl)propyl]thio}-1-ethanol was obtained as a colorless oil.

MS(FAB): 380(M+H)

$^1$H-NMR(CDCl$_3$) δ: 1.32(3H,t,J=6.8 Hz), 2.95(2H,t,J=6.4 Hz), 3.7–4.2(5H,m), 4.96(1H,d,J=14.0 Hz), 5.23(1H,d,J=14.0 Hz), 6.6–7.0(2H,m), 7.5–7.8(1H,m), 7.77(1H,s), 7.97 (1H,s).

Example 5

2-{[2-(Benzyloxy)-2-(2,4-difluorophenyl)-1,1-difluoro-3-(1H-1,2,4-triazol-1-yl)propyl]thio}-1-ethanol In a similar manner to Example 1 except that 2-(2,4-difluorophenyl)-1,1-difluoro-1[(2-methoxyethyl)thio]-3-(1H-1,2,4-triazol-1-yl)-2-propanol was replaced with 2-(2,4-difluorophenyl)-1,1-difluoro-1-[(2-hydroxyethyl)thio]-3-(1H-1,2,4-triazol-1-yl)-2-propanol and methyl iodide was replaced with benzyl chloride, the experiment was carried out, whereby 2-{[2-(benzyloxy)-2-(2,4-difluorophenyl)-1,1-difluoro-3-(1H-1,2,4-triazol-1-yl)propyl]thio}-1-ethanol was obtained as a colorless oil.

MS(FAB): 442(M+H)

$^1$H-NMR(CDCl$_3$) δ: 2.99(2H,t,J=6.4 Hz), 3.6–3.9(2H,m), 4.9–5.2(4H,m), 6.6–7.0(2H,m), 7.2–7.5(5H,m), 7.5–7.8(1H, m), 7.79(1H,s), 7.94(1H,s).

Example 6

2-{[2-(2,4-Difluorophenyl)-1,1-difluoro-2-methyoxy-3-(1H-1,2,4-triazol-1-yl)propyl]thio}ethyl acetate In a similar manner to Example 1 except that 2-(2,4-difluorophenyl)-1,1-difluoro-1-[(2-methoxyethyl)thio]-3-(1H-1,2,4-triazol-1-yl)-2-propanol was replaced with 2-{[(2,4-difluorophenyl)-1,1-difluoro-2-hydroxy-3-(1H-1,2,4-triazol-1-yl)propyl]thio}ethyl acetate, the experiment was carried out, whereby 2-{[2-(2,4-difluorophenyl)-1,1-difluoro-2-methoxy-3-(1H-1,2,4-triazol-1-yl)propyl]thio}ethyl acetate was obtained as a colorless oil.

MS(FAB): 408(M+H)

$^1$H-NMR(CDCl$_3$) δ: 2.08(3H,s), 3.42–3.54(2H,m), 3.75 (3H,s), 4.54(2H,t,J=6 Hz), 5.16(1H,d,J=15 Hz), 5.31(1H,d, J=15 Hz), 6.78–6.91(2H,m), 7.26–7.58(1H,m), 7.78(1H,s), 8.05(1H,s).

Example 7

Synthesis of 1-{2-(2,4-difluorophenyl)-3,3-difluoro-2-methoxy-3-[(2-methoxyethyl)sulfonyl]propyl}-1H-1,2,4-triazole To a solution of 1-{2-(2,4-difluorophenyl)-3,3-difluoro-2-methoxy-3-[(2-methoxyethyl)thio]propyl}-1H-1,2,4-triazole (800 mg, 2.12 mmol) in dichloromethane (10 ml), 85% m-chloroperbenzoic acid (1.25 g, 5.09 mmol) was added at room temperature, followed by stirring at room temperature for 3 hours. After the completion of the reaction, a saturated aqueous solution of sodium thiosulfate and a saturated aqueous solution of sodium bicarbonate were added to the reaction mixture and the resulting mixture was stirred. The dichloromethane solution was separated, washed with water, dried over magnesium sulfate and distilled off under reduced pressure. The residue so obtained was subjected to a silica gel column. From the chloroform elute fraction, 700 mg (yield: 81%) of 1-{2-(2,4-difluorophenyl)-3,3-difluoro-2-methoxy-3-[(2-methoxyethyl)sulfonyl]propyl}-1H-1,2,4-triazole were obtained as a yellow oil.

MS(FAB): 412(M+H)

$^1$H-NMR (CDCl$_3$) δ: 3.39(3H,s), 3.4–3.5(2H,m), 3.75 (3H,s), 3.88(2H,t,J=6.0 Hz), 5.18(1H,d,J=15.0 Hz), 5.31 (1H,d,J=15.0 Hz), 6.8–7.0(2H,m), 7.5–7.6(1H,m), 7.79(1H, s), 8.06(1H,s).

Example 8

1-[3-{[2-(Benzyloxy)ethyl]sulfonyl}-2-(2,4-difluorophenyl)-3,3-difluoro-2-methyoxypropyl]-1H-1,2,4-triazole In a similar manner to Example 7 except that (1-{2-(2,4-difluorophenyl)-3,3-difluoro-2-methoxy-3-[(2-methoxyethyl)thio]propyl}-1H-1,2,4-triazole was replaced with 1-[3-{[2-(benzyloxy)ethyl]thio}-2-(2,4-difluorophenyl)-3,3-difluoro-2-methyoxypropyl]-1H-1,2,4-triazole, the experiment was carried out, whereby 1-[3-{[2-(benzyloxy)ethyl]sulfonyl}-2-(2,4-difluorophenyl)-3,3-difluoro-2-methyoxypropyl]-1H-1,2,4-triazole was obtained as a colorless oil.

MS(FAB): 488(M+H)

$^1$H-NMR(CDCl$_3$) δ: 3.46(2H,t,J=6 Hz), 3.73(3H,s), 3.94 (2H,t,J=6 Hz), 4.56(2H,s), 5.18(2H,d,J=15 Hz), 5.35(2H,d, J=15 Hz), 6.67–6.95(2H,m), 7.33(5H,s), 7.51–7.75(1H,m), 7.77(1H,s), 8.05(1H,s).

Example 9

2-{[2-(2,4-Difluorophenyl)-1,1-difluoro-2-methoxy-3-(1H-1,2,4-triazol-1-yl)propyl]sulfonyl}-1-ethanol In a similar manner to Example 7 except that 1-{2-(2,4-difluorophenyl)-3,3-difluoro-2-methoxy-3-[(2-methoxyethyl)thio]propyl}-1H-1,2,4-triazole was replaced with 2-{[2-(2,4-difluorophenyl)-1,1-difluoro-2-methoxy-3-(1H-1,2,4-triazol-1-yl)propyl]thio}-1-ethanol, the experiment was carried out, whereby 2-{[2-(2,4-difluorophenyl)-1,1-difluoro-2-methoxy-3-(1H-1,2,4-triazol-1-yl)propyl]sulfonyl}-1-ethanol was obtained as colorless crystals.

Melting point: 108–110° C.

IR(KBr)ν$_{max}$cm$^{-1}$: 3200, 1614, 1500, 1336

MS(FAB): 398(M+H)

$^1$H-NMR(CDCl$_3$) δ: 2.95(1H,t,J=6.4 Hz), 3.3–3.6(2H,m), 3.75(3H,s), 4.0–4.4(2H,m), 3.18(1H,d,J=15.6 Hz), 5.32(1H, d,J=15.6 Hz), 6.6–7.0(2H,m), 7.4–7.7(1H,m), 7.79(1H,s), 8.07(1H,s).

Example 10

2-{[2-(2,4-Difluorophenyl)-2-ethoxy-1,1-difluoro-3-(1H-1,2,4-triazol-1-yl)propyl]sulfonyl}-1-ethanol In a similar manner to Example 7 except that (1-{2-(2,4-difluorophenyl)-3,3-difluoro-2-methoxy-3-[(2-methoxyethyl)thio]propyl}-1H-1,2,4-triazole was replaced with 2-{[2-(2,4-difluorophenyl)-2-ethoxy-1,1-difluoro-3-(1H-1,2,4-triazol-1-yl)propyl]thio}-1-ethanol, the experiment was carried out, whereby 2-{[2-(2,4-difluorophenyl)-2-ethoxy-1,1-difluoro-3-(1H-1,2,4-triazol-1-yl)propyl]sulfonyl}-1-ethanol was obtained as colorless crystals.

Melting point: 150–153° C.

IR(KBr)ν$_{max}$cm$^{-1}$: 3122, 1612, 1500, 1336

MS(FAB): 412(M+H)

$^1$H-NMR(CDCl$_3$) δ: 1.36(3H,t,J=6.8 Hz), 2.55(1H,br.s), 3.4–3.5(2H,m), 3.9–4.1(2H,m), 4.16(2H,t,J=5.4 Hz), 5.21 (1H,d,J=15.6 Hz), 5.30(1H,d,J=15.6 Hz), 6.7–7.9(1H,m), 7.5–7.6(1H,m), 7.78(1H,s), 8.02(1H,s).

Example 11

2-{[2-(Benzyloxy)-2-(2,4-difluorophenyl)-1,1-difluoro-3-(1H-1,2,4-triazol-1-yl)propyl]sulfonyl}-1-ethanol In a similar manner to Example 7 except that 1-{2-(2,4-difluorophenyl)-3,3-difluoro-2-methoxy-3-[(2-methoxyethyl)thio]propyl}-1H-1,2,4-triazole was replaced with 2-{[2-(benzyloxy)-2-(2,4-difluorophenyl)-1,1-difluoro-3-(1H-1,2,4-triazol-1-yl)propyl]thio}-1-ethanol, the experiment was carried out, whereby 2-{[2-(benzyloxy)-2-(2,4-difluorophenyl)-1,1-difluoro-3-(1H-1,2,4-triazol-1-yl)propyl]sulfonyl}-1-ethanol was obtained as colorless crystals.

Melting point: 144–145° C.

IR(KBr)ν$_{max}$cm$^{-1}$: 3191, 1614, 1500, 1340

MS(FAB): 474(M+H)

$^1$H-NMR(CDCl$_3$) δ: 2.50(1H,br.s), 3.3–3.5(2H,m), 4.11 (2H,t,J=5.4 Hz), 5.05(1H,d,J=9.8 Hz), 3.12(1H,d,J=9.8 Hz), 5.31(1H,d,J=15.6 Hz), 5.46(1H,d,J=15.6 Hz), 6.7–7.9(2H, m), 7.3–7.5(5H,m), 7.5–7.7(1H,m), 7.80(1H,s), 8.03(1H,s).

Example 12

2-{[2-(2,4-Difluorophenyl)-1,1-difluoro-2-methoxy-3-(1H-1,2,4-triazol-1-yl)propyl]sulfonyl}ethyl acetate In a similar manner to Example 7 except that 1-{2-(2,4-difluorophenyl)-3,3-difluoro-2-methoxy-3-[(2-methoxyethyl)thio]propyl}-1H-1,2,4-triazole was replaced with 2-{[2-(2,4-difluorophenyl)-1,1-difluoro-2-methoxy-3-(1H-1,2,4-triazol-1-yl)propyl]thio}ethyl acetate, the experiment was carried out, whereby 2-{[2-(2,4-difluorophenyl)-1,1-difluoro-2-methoxy-3-(1H-1,2,4-triazol-1-yl)propyl]sulfonyl}ethyl acetate was obtained as a colorless oil.

MS(FAB): 440(M+H)

$^1$H-NMR(CDCl$_3$) δ: 2.08(3H,s), 3.42–3.54(2H,m), 3.75 (3H,s), 4.54(2H,t,J=6 Hz), 5.16(1H,d,J=15 Hz), 5.31(1H,d, J=15 Hz), 6.78–6.91(2H,m), 7.26–7.58(1H,m), 7.78(1H,s), 8.05(1H,s).

Test 1: Antifungal Activity Against *Candida albicans* (In vitro)

To each well of a 96-well microtiter plate, 75 μl of a dilute medicament solution adjusted with a 10% fetal-bovine-serum added MEM medium (containing glutamine and a carbonate salt) were poured, followed by the addition of 75 μl of 4×10$^4$ cells/ml of *C. albicans* ATCC 44859 suspended with the same medium. They were incubated at 37° C. for 24 hours in a CO$_2$ gas incubator. After incubation, a morphological change of *C. albicans* was observed under an inverted microscope. The minimum medicament concentration permitting the apparent suppression of mycerial type growth compared with that of a medicament-free control was determined as a terminal point (ng/ml).

Test 2: Antifungal Activity Against *Aspergillus fumigatus* (In vitro)

To each well of a 96-well microtiter plate, 100 μl of a dilute medicament solution adjusted with 0.165M MOPS-containing RPMI 1640 (containing glutamine and phenol red, carbonate-salt free; pH 7) were poured, followed by the addition of 100 μl of 6.0×10⁴ conidia/ml of an *A. fumigatus* IFM 40808 spore suspension in the same medium. They were incubated at 35° C. for 24 hours. After incubation, the minimum medicament concentration permitting the apparent suppression of mycerial type growth compared with that of a medicament-free control was determined as an MIC value (μg/ml).

Test 3: Antifungal Activity Against *Aspergillus flavus* (In vitro)

To each well of a 96-well microtiter plate, 100 μl of a dilute medicament solution adjusted with 0.165M MOPS-containing RPMI 1640 (containing glutamine and phenol red, carbonate-salt free; pH 7) were poured, followed by the addition of 100 μl of 6.0×10⁴ conidia/ml of an *A. flavus* IFM 41935 spore suspension in the same medium. They were incubated at 35° C. for 24 hours. After incubation, the minimum medicament concentration permitting the apparent suppression of mycerial type growth compared with that of a medicament-free control was determined as an MIC value (μg/ml).

TABLE 1

| Test compound | Terminal point (ng/ml) C. albicans | MIC (μg/ml) A. fumigatus | MIC (μg/ml) A. flavus |
|---|---|---|---|
| Example 1 | 62.5 | 64 | >64 |
| Fluconazole | 250 | >128 | >128 |

Test 4: Antifungal Activity Against *Candida albicans* (In vivo)

After 4-week-old, male, ICR (CRJ: CD-1) mice were fasted for 6 hours, *C. albicans* IFM 40009 was inoculated to a tail vein of each of the mice to give an amount of 3.0×10⁶ cells/mouse, whereby infection was caused. A control group consisted of 10 mice, while a medicament-administered group consisted of 5 mice. The medicament was orally administered one hour after the inoculation of the fungus and then consecutively once a day 24 hours after the inoculation, four times in total, at 1.25 mg/kg each. The survival condition during 14 days after the infection was compared. In addition, the survival days of the control group and the medicament-administered group were detected by the Kaplan-Meier method (Cox mantel test).

TABLE 2

| Test compound | Survival days | Survival mice on Day 14 |
|---|---|---|
| Example 7 | 14.0*** | 5/5 |
| Example 9 | 14.0*** | 5/5 |
| Example 10 | 13.4*** | 4/5 |
| Example 12 | 14.0*** | 4/5 |
| Fluconazole | 9.6*** | 0/5 |
| Control | 4.1 | 0/10 |

***; $p < 0.001$

Example 13

Tablets

| Compound of Example 7 | 50 mg |
|---|---|
| Crystalline cellulose | 50 mg |
| Lactose | 50 mg |
| Hydroxypropyl cellulose | 18 mg |
| Magnesium stearate | 2 mg |
| Total | 170 mg |

In a manner known per se in the art, tablets having the above-described composition were prepared. The tablets can be formed as sugar coated tablets or film coated tablets as needed.

Example 14

Capsules

| Compound of Example 7 | 50 mg |
|---|---|
| Light silicic anhydride | 25 mg |
| Lactose | 100 mg |
| Starch | 50 mg |
| Talc | 25 mg |
| Total | 250 mg |

The above ingredients were filled in No. 1 capsules, whereby capsules were obtained.

Example 15

Granules

| Compound of Example 7 | 50 mg |
|---|---|
| Lactose | 600 mg |
| Corn starch | 200 mg |
| Carboxymethyl cellulose sodium | 20 mg |
| Hydroxypropyl cellulose | 130 mg |
| Total | 1000 mg |

In a manner known per se in the art, granules having the above-described composition were prepared.

Example 16

Powders

| Compound of Example 7 | 50 mg |
|---|---|
| Light silicic anhydride | 20 mg |
| Precipitated calcium carbonate | 10 mg |
| Lactose | 250 mg |
| Starch | 70 mg |
| Total | 400 mg |

In a manner known per se in the art, powders having the above-described composition were prepared.

Example 17

Injection

| Compound of Example 7 | 5 mg |
|---|---|
| Hydrogenated castor oil | 85 mg |
| Propylene glycol | 60 mg |
| Glucose | 50 mg |
| Distilled water for injection | q.s. |
| Total | 1 ml |

In a manner known par se in the art, an injection having the above-described composition was prepared.

Example 18
Intravenous drip infusion

| | |
|---|---|
| Compound of Example 7 | 50 mg |
| Hydrogenated castor oil | 5 g |
| Propylene glycol | 10 mg |
| Glucose | 14.5 mg |
| Distilled water for injection | q.s. |
| Total | 100 ml |

An intravenous drip infusion having the above-described composition was prepared in a manner known per se in the art.

Industrial Applicability

The triazole derivative or salt thereof according to the present invention has strong antimycotic action, and an antimycotic comprising the derivative or salt as an effective ingredient is useful for the prevention and treatment of mycotic infections of mammary animals including human.

What is claimed is:

1. A triazole compound of the formula:

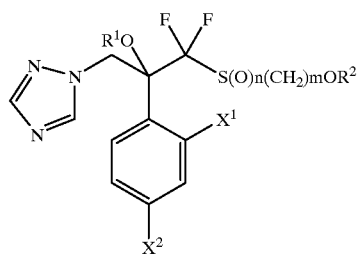

(1)

wherein $R^1$ is a linear or branched $C_{1-6}$-alkyl or $C_{7-11}$-aralkyl group, $R^2$ is hydrogen, linear or branched $C_{1-6}$-alkyl, a phenyl-$C_{1-5}$-alkyl or $C_{2-10}$-acyl, $X^1$ and $X^2$ are the same or different and each independently is hydrogen, halogen or trifluoromethyl, and is 0, 1 or 2 and m is an integer of 1–5, or a salt thereof.

2. The triazole compound of claim 1, wherein said alkyl of groups $R^1$ and $R^2$ is methyl, ethyl, n-propyl, isopropyl, n-butyl, t-butyl, pentyl or hexyl.

3. The triazole compound of claim 1, wherein said $C_{2-10}$-acyl is $C_{2-10}$-alkanoyl or $C_{7-10}$-aroyl.

4. The triazole compound of claim 2, wherein $R^1$ is methyl, ethyl or benzyl, $R^2$ is hydrogen, methyl, benzyl or acetyl and $X^1$ and $X^2$ are each fluorine.

5. A method of treating a mycotic infection, comprising:

administering to a subject suffering from a mycotic infection an effective amount of the triazole compound of claim 1.

6. An anti-mycotic pharmaceutical composition, comprising:

an effective amount of a triazole compound or salt thereof as claimed in claim 1 and a pharmacologically acceptable carrier.

7. The anti-mycotic pharmaceutical composition of claim 6, wherein the amount of the composition administered to an adult subject is such that the dose of compound administered ranges from 0.1–10 mg/day.

* * * * *